| United States Patent [19] | [11] Patent Number: 4,463,181 |
| Morwick et al. | [45] Date of Patent: Jul. 31, 1984 |

[54] PROCESS FOR REMOVING SULFONYL GROUPS FROM BENZIMIDAZOLE ISOMERS

[75] Inventors: Tina M. Morwick, Beech Grove; James H. Wikel, Greenwood, both of Ind.

[73] Assignee: Eli Lilly and Company, Indianapolis, Ind.

[21] Appl. No.: 477,476

[22] Filed: Mar. 21, 1983

Related U.S. Application Data

[63] Continuation-in-part of Ser. No. 366,759, Apr. 8, 1982, abandoned.

[51] Int. Cl.$^3$ .............................................. C07D 235/30
[52] U.S. Cl. ................................................. 548/306
[58] Field of Search ................. 542/429, 467; 548/306

[56] References Cited

U.S. PATENT DOCUMENTS

| 3,825,537 | 7/1974 | Haugwitz et al. | 260/243 R |
| 4,008,243 | 2/1977 | Wikel et al. | 548/306 |
| 4,018,790 | 4/1977 | Paget et al. | 548/306 |
| 4,118,573 | 10/1978 | Paget et al. | 548/306 |
| 4,118,742 | 10/1978 | Paget et al. | 548/306 |
| 4,150,028 | 4/1979 | Paget et al. | 260/306.7 T |
| 4,174,454 | 11/1979 | Paget et al. | 548/306 |
| 4,196,125 | 4/1980 | Paget et al. | 548/141 |
| 4,216,313 | 8/1980 | Paget et al. | 544/55 |
| 4,230,868 | 10/1980 | Paget et al. | 548/306 |

OTHER PUBLICATIONS

Sidgwick, *The Organic Chemistry of Nitrogen*, (1966) p. 251.
Smith, *The Chemistry of Open-Chain Organic Nitrogen Compounds*, vol. I, (1965) pp. 188-189.
Wright, Chem. Reviews, 48, 486-487 (1951).
Price, et al. "Some Sulfonamide Derivatives of 2-Aminobenzimidazole." J. Org. Chem. 12, 269-274 (1947).

*Primary Examiner*—Robert W. Ramsuer
*Attorney, Agent, or Firm*—Karen B. Dow; Arthur R. Whale

[57] ABSTRACT

This invention discloses a process for removing a sulfonyl group from the 1-position of a benzimidazole to allow conversion of 2-amino-1,5-substituted-benzimidazole compounds into 2-amino-1,6-substituted-benzimidazole compounds. The 5-isomer is reacted with an alkali metal hydroxide or carbonate in an inert aqueous organic solvent system. The reaction is acidified to precipitate the base and form the intermediate benzimidazole tautomer. The intermediate is then reacted with a sulfonyl acylating agent or a haloalkyl isothiocyanate to form a mixture of 2-amino-1,5(6)-substituted-benzimidazole compounds. This invention also discloses the same process for removing a sulfonyl group from the 1-position of a benzimidazole to allow conversion of 2-amino-1,6-substituted-benzimidazole compounds into 2-amino-1,5-substituted-benzimidazole compounds.

9 Claims, No Drawings

PROCESS FOR REMOVING SULFONYL GROUPS FROM BENZIMIDAZOLE ISOMERS

CROSS REFERENCE TO RELATED APPLICATIONS

This is a continuation-in-part of application Ser. No. 366,759, filed Apr. 8, 1982 now abandoned.

BACKGROUND OF THE INVENTION

This invention describes a process for removing a sulfonyl group from the 1-position of a benzimidazole to allow conversion of the 5-isomer into the 6-isomer and also conversion of the 6-isomer into the 5-isomer.

2-Amino-1,5(6)-substituted-benzimidazole compounds inhibit the growth of certain viruses, such as rhinoviruses, polio (types I, II, III), Coxsackie (A9, A21, B5), echo virus (strains 1, 2, 3, 4), and Mengo virus. Although both the 5- and 6-isomers are useful as antiviral agents, the 6-substituted-2-amino-benzimidazole is generally the more active isomer.

Certain sulfonylbenzimidazole compounds are disclosed in U.S. Pat. Nos. 4,118,742 and 4,174,454. The preparation of these reference compounds follows the methods disclosed in U.S. Pat. Nos. 4,018,790 and 4,118,573. Both of these patents reveal the reaction of a benzimidazole compound and a sulfonyl chloride compound in an organic solvent in the presence of a base.

Thiazolinyl and thiazinyl benzimidazole compounds are prepared by the reaction of a 1-unsubstituted-benzimidazole with a haloalkyl isothiocyanate in an organic solvent in the presence of a base, as described in U.S. Pat. Nos. 4,008,243 and 4,150,028. The references also discuss the compounds use as antiviral agents.

In Chemical Reviews, 48, 397–541 (1951), John B. Wright reports the imidazole ring of benzimidazole compounds is cleaved by an acid halide and water, forming a diamine compound.

Charles Price and Robert Reitsema in "Some Sulfonamide Derivatives of 2-Aminobenzimidazole," Journal of Organic Chemistry, 12, 269–274 (1947) describe the formation of 2-aminobenzimidazole-3-nitrobenzenesulfonate by treating 1-(3-nitrophenylsulfonyl)-2-aminobenzimidazole with sodium hydroxide and acetic acid.

SUMMARY OF THE INVENTION

This invention concerns a process for removing a sulfonyl group from the 1-position of a benzimidazole to allow conversion of 2-amino-1,5-substituted-benzimidazole compounds into a mixture of 5- and 6-substituted isomers, from which the preferred 6-isomer is recovered. The 5-isomer also formed then can be recycled through this process to form more 5- and 6-isomers. This invention also discloses the same process for removing a sulfonyl group from the 1-position of a benzimidazole to allow conversion of the 6-isomer into the 5-isomer.

A benzimidazole compound of the formula O

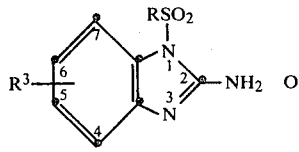

is reacted with an alkali metal hydroxide or carbonate in an inert aqueous organic solvent at a temperature from about 20° C. to about 100° C. to form a tautomeric benzimidazole of the formula II.

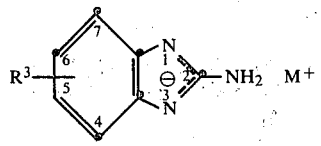

The tautomer (II) then can be reacted with a sulfonyl halide or a haloalkyl isothiocyanate to form a mixture of the 5- and 6-isomers.

In particular, the 5-isomer compound of the formula I

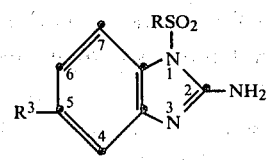

can be reacted to form the tautomeric benzimidazole of the formula II.

Another aspect of this invention is removing a sulfonyl group from the 1-position of a benzimidazole to allow conversion of 2-amino-1,6-substituted-benzimidazole compounds into 2-amino-1,5-substituted-benzimidazole compounds. The 6-isomer compound of the formula III

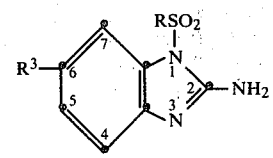

is reacted in the same manner as the 5-isomer to form the tautomeric benzimidazole of the formula II.

DETAILED DESCRIPTION AND PREFERRED EMBODIMENTS

This invention discloses a process for removing a sulfonyl group from the 1-position of a benzimidazole to allow conversion of 2-amino-1,5-substituted-benzimidazole compounds into a mixture of 5- and 6-substituted isomers, form which the preferred 6-isomer is recovered. The 5-isomer also formed then can be recycled through this process to form more 5-and 6-isomers. This invention also discloses the same process for removing a sulfonyl group from the 1-position of a benzimidazole to allow conversion of the 6-isomer into the 5-isomer.

The 5- and 6-isomer can be represented by formula O

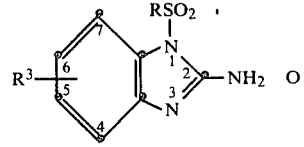

A 1-substituted-2-amino-5-substituted-benzimidazole of the formula I

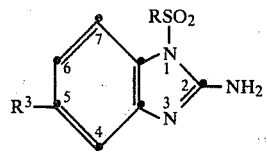

is reacted with an alkali metal hydroxide or carbonate in an inert aqueous organic solvent system to form a tautomeric benzimidazole of the formula II.

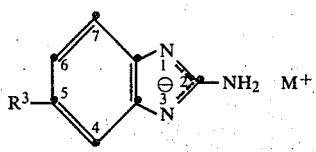

The tautomer (II) then can be reacted with a sulfonyl halide of the formula $R^1SO_2X$; or a haloalkyl isothiocyanate of the formula $X(CH_2)_nNCS$, optionally substituted on the carbon chain with $R^5$; to form a mixture of 5- and 6-isomers.

The desired 2-amino-1,6-substituted-benzimidazole is of the formula IV.

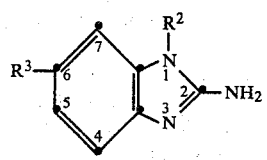

A 1-substituted-2-amino-6-substituted-benzimidazole of the formula III

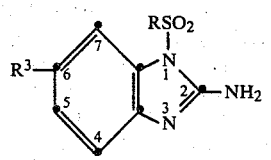

is reacted with an alkali metal hydroxide or carbonate in an inert aqueous organic solvent system to form a tautomeric benzimidazole of the formula II.

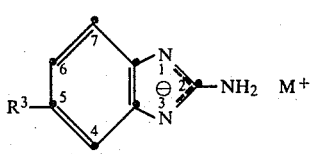

The tautomer (II) the can be reacted with a sulfonyl halide of the formula $R^1SO_2X$, or a haloalkyl isothiocyanate of the formula $X(CH_2)_nNCS$, optionally substituted on the carbon chain with $R^5$; to form a mixture of 5- and 6-isomers.

The desired 2-amino-1,5-substituted-benzimidazole is of the formula V.

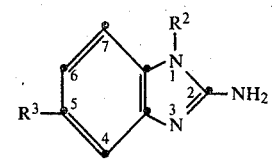

In the above formulas:
R is $C_1$–$C_5$ alkyl, $C_3$–$C_7$ cycloalkyl, furyl, or thienyl;
$R^1$ is $C_1$–$C_5$ alkyl, $C_3$–$C_7$ cycloalkyl, phenyl, furyl, or thienyl;
$R^2$ is $R^1SO_2$ or

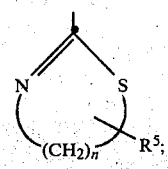

$R^3$ is $C_1$–$C_4$ alkyl, $C_1$–$C_4$ alkoxy, halo, nitro, $C_1$–$C_4$ alkylthio, phenylthio, phenoxy, carboxy, methylsulfonyl, trifluoromethyl,

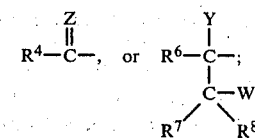

$R^4$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)-ethyl, thienyl, benzyl, phenyl, or mono-substituted phenyl wherein said phenyl substituent is selected from the group consisting of $C_1$–$C_4$ alkyl, $C_1$–$C_4$ alkoxy, chloro, bromo, iodo, nitro, and trifluoromethyl;
$R^5$ is hydrogen, $C_1$–$C_3$ alkyl, benzyl, or phenyl;
$R^6$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, phenyl, or mono-substituted phenyl, wherein said phenyl substituent is selected from the group consisting of $C_1$–$C_4$ alkyl, $C_1$–$C_4$ alkoxy, chloro, bromo, iodo, nitro, and trifluoromethyl;
$R^7$ and $R^8$ independently are hydrogen, halo, cyano, hydroxymethyl, nitro,

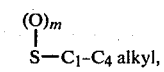

$CH_2R^9$, $COR^9$, phenyl or mono-substituted phenyl, wherein said phenyl substituent is selected from the group consisting of $C_1$–$C_4$ alkyl, $C_1$–$C_4$ alkoxy, chloro, bromo, iodo, nitro, and trifluoromethyl;
$R^9$ is hydroxy, $C_1$–$C_4$ alkoxy, halo, $C_3$–$C_6$ cycloalkyl $C_1$–$C_4$ alkoxy, or $(O$—$C_1$–$C_4$ alkyl$)_p$ $NR^{10}R^{11}$ wherein $R^{10}$ and $R^{11}$ independently are hydrogen or $C_1$–$C_4$ alkyl;
Z is oxygen, $C_1$–$C_7$ alkylidene, or $C_1$–$C_4$ alkoxyimino;
X is chloro or bromo;
Y is hydrogen, and W is hydroxy, or together Y and W form a bond;
$M^+$ is an alkali metal cation or a hydronium ion;
m is 0, 1, or 2;
n is 2 or 3; and p is 0 or 1.

Preferred substituent groups in this process are those wherein;

R and $R^1$ are isopropyl;
$R^2$ is $R^1SO_2$;
$R^3$ is

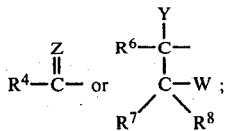

$R^4$ and $R^6$ are phenyl or mono-substituted phenyl; and
Z is oxygen or $C_1-C_7$ alkylidene.

Even more preferred are these in which:
$R^4$ and $R^6$ are phenyl;
Y and W together form a bond; and
Z is oxygen or ethylidene.

The following definitions refer to the various terms used throughout this disclosure. The term "furyl" refers to the furan radical attached at the alpha or beta position. The term "thienyl" refers to the thiophene radical attached at the 2- or 3- position.

The term "thiazolinyl" or "thiazolin-2-yl" refers to the 4,5-dihydrothiazole radical attached at the 2-position, which may have a substituent group ($R^5$) at the 4- or 5- positions. The term "thiazinyl" or "thiazin2-yl" refers to 5,6-dihydro-4H-1,3-thiazine radical attached at the 2-position, which may have a substituent group ($R^5$) at the 4-, 5-, or 6-positions. The substituent group ($R^5$) can be methyl, ethyl, propyl, benzyl, or phenyl.

The term "$C_1-C_7$ alkyl" refers to the straight and branched aliphatic radicals of one to seven carbon atoms including methyl, ethyl, propyl, isopropyl, butyl, isobutyl, sec-butyl, tert-butyl, pentyl, isopentyl, sec-pentyl, 1,2-dimethylpropyl, 1,1-dimethylpropyl, neopentyl, hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl (5-methylhexyl), sec-heptyl (1-methylhexyl), 1-ethylpentyl, 2,2-dimethylpentyl, 3,3-dimethylpentyl, 4,4-dimethylpentyl, 1,2-dimethylpentyl, 1,4-dimethylpentyl, 1,2,3-trimethylbutyl, 1,1,2-trimethylbutyl, 1,1,3-trimethylbutyl, and the like. The term $C_1-C_7$ alkyl includes within its definition the terms "$C_1-C_3$ alkyl", "$C_1-C_4$ alkyl", and "$C_1-C_5$ alkyl".

The term "$C_3-C_7$ cycloalkyl" refers to the saturated alicyclic rings of three to seven carbon atoms, such as cyclopropyl, methylcyclopropyl, cyclobutyl, cyclopentyl, cyclohexyl, 1-, 2-, 3-, or 4-methylcyclohexyl, and cycloheptyl.

The term "$C_1-C_4$ alkoxy" refers to the alkyl radicals of one to four carbon atoms attached to the remainder of the molecule by oxygen and includes methoxy, ethoxy, propoxy, and the like.

The term

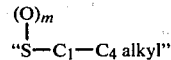

refers to alkyl radicals of one to four carbon atoms attached to a thio, sulfinyl, or sulfonyl group. Examples of such groups include methylthio, ethylthio, isobutylthio, ethylsulfinyl, isobutylsulfinyl, isopropylsulfonyl, n-butylsulfonyl, tert-butylsulfonyl, and the like.

The term "$C_1-C_7$ alkylidene" refers to divalent organic radicals of one to seven carbon atoms derived from the corresponding aliphatic hydrocarbons in which two hydrogen atoms are taken from the same carbon atom including ethylidene, propylidene, butylidene, pentylidene, and the like.

The terms "halo" and "halide" refer to chloro, bromo, chloride, and bromide.

The term "alkali metal hydroxide or carbonate" refers to sodium or potassium hydroxide, sodium or potassium carbonate, and the like. The base of choice is sodium hydroxide. Any amount of base can be used; but for maximum yield one equivalent of base for every equivalent of benzimidazole is preferred.

The symbol "$M^+$" refers to a hydronium ion or an alkali metal cation, which is the cation of the inorganic base used to remove the sulfonyl group at the 1-position. Therefore, $M^+$ is usually a sodium or potassium cation and is preferably sodium.

The inert aqueous organic solvent system is a combination of water and a water-miscible solvent. The ratio of water to solvent should be from about 10/90 to about 75/25. A nonhydroxylic solvent (one that does not contain hydroxyl groups) is required unless the benzimidazole anion is isolated before sulfonation. If the benzimidazole is isolated, then hydroxylic solvents, such as carbinols, can be used.

Suitable nonhydroxylic solvents include acetone, dimethoxyethane (glyme, DME), tetrahydrofuran (THF), tertiary amides, such as N,N-dimethylformamide (DMF), and the like. The preferred solvent is acetone. Any mixture of the above solvents may be used in place of a single solvent and the addition of an immiscible solvent is permitted as long as the overall solvent combination is water-miscible.

The reaction should be carried out at a temperature from about 20° C. to about 100° C., preferably at the reflux temperature of the solvent system employed.

If desired, the process can be stopped at the formation of the tautomer. To form the benzimidazole tautomer, the 5- or 6-isomer is reacted with an alkali metal hydroxide or carbonate in an inert aqueous organic solvent system. Then it can be isolated. If greater than 1 equivalent of hydroxide or carbonate was used to remove the sulfonyl group, the solution containing the benzimidazole tautomer must be acidified to isolate its free base.

After the sulfonyl group is removed leaving the benzimidazole anion, a substituent then can be added at the 1-position to form a mixture of 1,5- and 1,6-substituted-benzimidazole compounds. The new substituent can be added by two methods.

The first method is shown in U.S. Pat. No. 4,008,243. However, the benzimidazole must be isolated before this method can be used. Isolation is achieved by adding an acid to the solution containing the benzimidazole tautomer, thereby, causing the benzimidazole to precipitate. The benzimidazole is then placed in an aprotic solvent, such as aromatic hydrocarbons, e.g. benzene, toluene, or xylene, or ethers such as ethyl ether, glyme or tetrahydrofuran. The benzimidazole salt is formed in solution and is then reacted with added sulfonyl halide ($R^1SO_2X$) or haloalkyl isothiocyanate ($X(CH_2)_nNCS$) to form a mixture of 1,5- and 1,6-substituted-benzimidazole compounds.

The second method of adding a substituent at the 1-position of the benzimidazole anion is described in application, Ser. No. 366,883, filed Apr. 8, 1982 now U.S. Pat. No. 4,434,288. In this method, the benzimidazole does not have to be isolated before addition, if a nonhydroxylic solvent was used to remove the sulfonyl group. The reactant, sulfonyl halide or haloalkyl isothiocyanate, is added to the reaction vessel containing the benzimidazole anion. Therefore, the removal of the sulfonyl group and the addition of a different substituent can be performed in a single reaction vessel through this method.

The product of the addition reaction is a mixture of 1,5- and 1,6-substituted-benzimidazole compounds, which can be separated and isolated. In those instances where the product precipitates, it may be separated from the reaction mixture by filtration. Alternatively, the reaction mixture may be concentrated to induce crystallization. Or the reaction mixture can be evaporated to dryness and the residue dissolved in a suitable solvent (such as acetone or methanol) to separate and remove any insoluble material. Then the acetone or methanol solution containing the substituted benzimidazole compound is concentrated to crystallize the product or it is evaporated to give a second residue. The second residue is dissolved in a solvent, such as methanol, and the benzimidazole compound is recovered from the solvent by crystallization.

The addition process usually provides about a 1:1 mixture of 1,5- and 1,6-substituted-benzimidazole isomers. The isomers can be separated by fractional crystallization or by column chromatography. The 6-isomer usually crystallizes first from a solution of the two isomers. The isomers can be identified by their nuclear magnetic resonance spectra in the phenyl proton region (7.0 to 8.3 ppm).

It should be noted that when $R^7$ and $R^8$ in the above general formula are different, the compounds formed exist as cis and trans isomers. The cis and trans isomers of the benzimidazoles provided herein are represented by the general formulas:

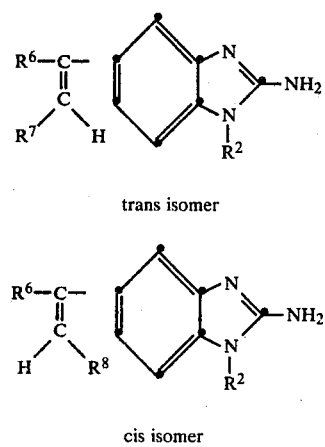

Since both the cis and trans benzimidazoles are potent antiviral agents, they can be utilized in the treatment of viral infections either alone or as a mixture.

Isolation of pure cis and pure trans benzimidazoles generally is accomplished by chromatography or by crystallization or fractional crystallization from solvent such as methanol, ethanol, acetone, or the like. The trans (E) isomers appear slightly more active than the cis (Z) compounds, and therefore are preferred over the cis (Z) isomers.

The collected 5- or 6-isomer can be recycled through the claimed removal process, if the substituent at the 1-position is a sulfonyl group. Thiazinyl and thiazolinyl groups cannot be removed by this process, and therefore, cannot be recycled.

The preparation of the benzimidazole and sulfonyl halide starting materials for use in the disclosed process is taught in U.S. Pat. Nos. 4,018,790 and 4,118,573. The preparation of haloalkyl isothiocyanates is taught in U.S. Pat. No. 4,008,243. Such teachings are incorporated herein be reference.

The following examples are illustrative of this invention, but are not to be considered as limitations on it.

EXAMPLE 1

2-amino-5(6)-methoximephenylbenzimidazole

A slurry of 5.6 g (0.015 moles) of 2-amino-6-methoximephenyl-1-isopropylsulfonylbenzimidazole was heated on a steam bath in 50 ml of acetone and 50 ml of water with 16 ml of 1 N sodium hydroxide. The heat was continued to remove the acetone by boiling. An oil developed that would not crystallize, so acetone was added to dissolve the oil in the reaction media. The product was precipitated with water, then filtered, and then washed with water. The yield of product was 3.5 g or 88%. There were the expected mass spectrum ions at m/e=266, and 235, while the $pK_a$ was 6.38–13.8.

The NMR indicated that two isomers were present as indicated by methoxy resonances.

The following elemental analysis was obtained:
Calculated for $C_{15}H_{14}N_4O.7/4\ H_2O$:
Theory: C, 60.60; N, 5.72; N, 18.85.
Found: C, 60.51; H, 5.42; N, 18.64.

EXAMPLE 2

2-amino-5(6)-(ethylidenebenzyl)benzimidazole

A slurry of 4.6 g (0.015 moles) of 2-amino-1-isopropylsulfonyl-6-(ethylidenebenzyl)benzimidazole was heated in 50 ml of acetone and 50 ml of water with 16 ml of 1 N sodium hydroxide on a steam bath. The heating was continued to remove the acetone. Afterwards the solution was cooled to room temperature with stirring. When the cleavage was complete, the precipitate title compound was filtered and washed with water.

The yield was 2.75 g (74%). The mass spectrum showed the expected molecular ion at m/e=249, 172 (loss of -phenyl), 115 (representing -benzimidazole ring). pH 9.06, $pK_a$ 6.98 (66% DMF/H₂O).

The following elemental analysis was obtained:
Calculated for $C_{16}H_{15}N_3$: Theory: C, 77.08; H, 6.06; N, 16.85.
Found: C, 77.33; H, 6.12; N, 16.57.

| NMR (DMSO) | | | |
|---|---|---|---|
| δ | H's | Multiplicity | Group |
| 1.66 | 3 | doublet | =CH—CH₃ |
| 1.83 | | doublet | |
| 6.0 | 1 | doubled quartet | =CH—CH₃ |
| 6.6–7.6 | 8 | aromatic | |
| | 2 | NH multiplet | |

EXAMPLE 3 trans-2-amino-5(6)-(ethylidenebenzyl)benzimidazole

A slurry of 1 g (0.0028 moles) of trans-2-amino-1-isopropylsulfonyl-6-(ethylidenebenzyl)benzimidazole was heated in 10 ml of acetone and 10 ml of water with 3 ml of 1 N sodium hydroxide on a steam bath. The heating was continued to remove the acetone. Afterwards the solution was cooled to room temperature with stirring. When the cleavage was complete, the precipitate title compound was filtered and washed with water.

The yield was 330 mg. (47%) and the mass spectrum showed the expected molecular ion at m/e=249, 172 (loss of -phenyl), 115 (representing -benzimidazole ring). pH 8.61, $pK_a$ 7.05 (66% DMF/$H_2O$).

The following elemental analysis was obtained:
Calculated for $C_{16}H_{15}N_3$:
Theory: C, 77.08; H, 6.06; N, 16.85.
Found: C, 76.82; H, 6.13; N, 16.63.

| NMR (DMSO) | | | |
|---|---|---|---|
| δ | H's | Multiplicity | Group |
| 1.66 | 3 | doublet | =CH—$CH_3$ |
| 6.0 | 1 | quartet | =CH—$CH_3$ |
| 6.2 | 2 | broad singlet | —$NH_2$ |
| 6.6–7.5 | 8 | multiplet | aromatic |

EXAMPLE 4

2-amino-5(6)-benzoylbenzimidazole

A slurry of 50 g of 2-amino-1-isopropylsulfonyl-5-benzoylbenzimidazole was heated in 300 ml of acetone and 500 ml of water with 350 ml of 1N sodium hydroxide on a steam bath for two hours. The heating was continued to remove the acetone. Afterwards the solution was cooled to room temperature with stirring. When the cleavage was complete, the precipitate title compound was filtered and washed with water. m/e=237, 160, 105, 77.

| NMR (DMSO) | | |
|---|---|---|
| δ | H's | Multiplicity |
| 6.8 | 3 | broad singlet |
| 7.2–8.2 | 8 | multiplet |

EXAMPLE 5

2-amino-5(6)-(propanoyl)benzimidazole

A slurry of 1 g (0.003 moles) of 2-amino-1-isopropylsulfonyl-6-propanoylbenzimidazole was heated in 10 ml of water and 10 ml of acetone with 4 ml of 1 N sodium hydroxide on a steam bath for about 4 hours. After the acetone was boiled off, the solution was diluted with water and neutralized. The precipitate was extracted with ethyl acetate, then dried with magnesium sulfate, and concentrated in vacuo.

The yield was 0.320 mg/(56%) and the mass spectrum showed the expected molecular ions at m/e=189 and 160. The NMR spectrum was consistent with the structure.

EXAMPLE 6

2-amino-5(6)-(methylidenebenzyl)benzimidazole

A slurry of 5.1 g (0.015 mole) of 2-amino-1-isopropylsulfonyl-6-(methylidenebenzyl)benzimidazole was heated in 50 ml of acetone and 50 ml of water with 16 ml of 1N sodium hydroxide on a steam bath. After the acetone was boiled off, the solution was cooled to room temperature with stirring. When the cleavage was complete, the precipitate title compound was filtered and washed with water.

The yield was 3.25 g (92%) and the mass spectrum showed the expected molecular ion at m/e=235. pH 8.98, $pK_a$ 6.8 (66% DMF/$H_2O$).

The following elemental analysis was obtained:
Calculated for $C_{15}H_{13}N_3$:
Theory: C, 76.57; H, 5.57; N, 17.86.
Found: C, 78.86; H, 5.91; N, 17.66.

| NMR (DMSO) | | | |
|---|---|---|---|
| δ | H's | Multiplicity | Group |
| 5.4 | 2 | doubled doublet | =$CH_2$ |
| 6.4 | 3 | broad singlet | |
| 6.8–7.5 | 8 | aromatic multiplet | |

EXAMPLE 7

2-amino-5(6)-benzoylbenzimidazole

A slurry of 2.5 g (0.0075 moles) of 2-amino-1-isopropylsulfonyl-5(6)-benzoylbenzimidazole was heated in 25 ml of water and 25 ml of acetone with 16 ml of 1N sodium hydroxide until complete solution of the reactants occurred. To the solution was added 0.9 ml (0.01 moles) of methyl chloroformate. The reaction mixture was then heated in a steam bath until the acetone boiled off. The resultant precipitate was filtered to provide 1.43 g of the product. pH 9.85, $pK_a$ 5.65, 13.0. m/e=237, 160, 105, 77.

| NMR (DMSO) | | |
|---|---|---|
| δ | H's | Multiplicity |
| 6.8 | 3 | broad singlet |
| 7.2–8.2 | 8 | multiplet |

EXAMPLE 8

2-amino-5(6)-benzoylbenzimidazole

The procedure of Example 7 was repeated using the same quantities of materials, but the reaction mixture was not heated and only allowed to stand at room temperature overnight (16 hours). The mixture was diluted with water and the precipitate collected to yield 1.39 g (73%) of the product. An NMR and mass spectra identical with Example 7 were obtained. pH 9.8, $pK_a$ 5.7, 13.15. (66% DMF/$H_2O$).

The following elemental analysis was obtained:
Calculated for $C_{14}H_{11}N_3O$:
Theory: C, 70.87; H, 4.67; N, 17.71.
Found: C, 71.15; H, 4.95; N, 17.74.

EXAMPLE 9

2-amino-5(6)-benzoylbenzimidazole

A slurry of 5 g (0.015 moles) of 2-amino-1-isopropylsulfonyl-(6)-benzoylbenzimidazole in 50 ml of water and 50 ml of tetrahydrofuran with 18 ml of 1N sodium hydroxide was heated on a steam bath. After a complete solution was formed, the reaction mixture was cooled to room temperature and 1N hydrochloric acid was added. The solution was concentrated under reduced pressure. The residue was titurated with methanol/water. The white solid was filtered and TLC (ethyl acetate) indicated the desired product. Yield=2.36 g (66%). m/e=237, 160, 105, 77. pH 7.2, pK$_a$ 5.6, 13.0. (66% DMF/H$_2$O).

| NMR (DMSO) | | |
|---|---|---|
| δ | H's | Multiplicity |
| 5.6 | 2 | broad singlet |
| 6.8 | 1 | broad singlet |
| 7.2–8.0 | 8 | multiplet |

EXAMPLE 10
2-amino-5(6)-benzoylbenzimidazole

A slurry of 20 g (0.058 moles) of 2-amino-1-isopropyl-sulfonyl-5(6)-benzoylbenzimidazole in 150 ml of water with 70 ml of 1N sodium hydroxide was heated on a steam bath. After one hour 50 ml of acetone was added and heating continued for 3 hours. The reaction mixture was held overnight (16 hours) at room temperature, then filtered, extracted 3 times with 200 ml of ethyl acetate, washed with brine, treated with carbon, and concentrated under reduced pressure. The residue was titurated with methanol and TLC (ethyl acetate) indicated the desired product. Yield 5.2 g m/e32 237, 160, 105, 77. pH 8.59, pK$_a$ 5.41. 12.89. (66% DMF/H$_2$O).

| NMR (DMSO) | | |
|---|---|---|
| δ | H's | Multiplicity |
| 6.8 | 2 | broad singlet |
| 7.2–7.8 | 8 | multiplet |
| 11 | 1 | broad singlet |

We claim:
1. A process for removing a sulfonyl group of the formula RSO$_2$ from the 1-position of a benzimidazole compound which consists essentially of
reacting a benzimidazole compound of the formula O

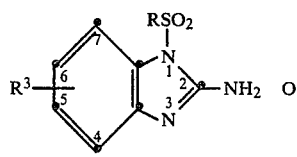

with an alkali metal hydroxide or carbonate in an inert aqueous organic solvent system selected from acetone, dimethoxy ethane, tetrahydro furan and tertiary amides at a temperature from about 20° C. to about 100° C., wherein
R is C$_1$–C$_5$ alkyl, C$_3$–C$_7$ cycloalkyl, phenyl, furyl, or thienyl;
R$^3$ is C$_1$–C$_4$ alkyl, C$_1$–C$_4$ alkoxy, halo, nitro, C$_1$–C$_4$ alkylthio, phenylthio, phenoxy, carboxy, methylsulfonyl, trifluoromethyl,

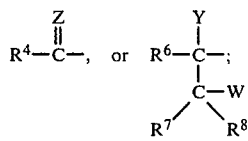

R$^4$ is hydrogen, C$_1$–C$_7$ alkyl, C$_3$–C$_7$ cycloalkyl, (C$_3$–C$_7$ cycloalkyl)methyl, 1-(C$_3$–C$_7$ cycloalkyl)ethyl, thienyl, benzyl, phenyl, or mono-substituted phenyl wherein said phenyl substituent is selected from the group consisting of C$_1$–C$_4$ alkyl, C$_1$–C$_4$ alkoxy, chloro, bromo, iodo, nitro, and trifluoromethyl;
R$^6$ is hydrogen, C$_1$–C$_7$ alkyl, C$_3$–C$_7$ cycloalkyl, (C$_3$–C$_7$ cycloalkyl)methyl, 1-(C$_3$–C$_7$ cycloalkyl)ethyl, phenyl, or mono-substituted phenyl, wherein said phenyl substituent is selected from the group consisting of C$_1$–C$_4$ alkyl, C$_1$–C$_4$ alkoxy, chloro, bromo, iodo, nitro, and trifluoromethyl;
R$^7$ and R$^8$ independently are hydrogen, halo, cyano, hydroxymethyl, nitro,

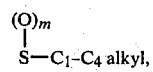

CH$_2$R$^9$, COR$^9$, phenyl or mono-substituted phenyl, wherein said phenyl substituent is selected from the group consisting of C$_1$–C$_4$ alkyl, C$_1$–C$_4$ alkoxy, chloro, bromo, iodo, nitro, and trifluoromethyl;
R$^9$ is hydroxy, C$_1$–C$_4$ alkoxy, halo, C$_3$–C$_6$ cycloalkyl C$_1$–C$_4$ alkoxy, or (O—C$_1$–C$_4$ alkyl)$_p$ NR$^{10}$R$^{11}$ wherein R$^{10}$ and R$^{11}$ independently are hydrogen or C$_1$–C$_4$ alkyl;
Z is oxygen, C$_1$–C$_7$ alkylidene, or C$_1$–C$_4$ alkoxyimino;
Y is hydrogen, and W is hydroxy, or together Y and W form a bond;
m is 0, 1, or 2; and
p is 0 or 1.
2. The process of claim 1 wherein the alkali metal hydroxide or carbonate is sodium hydroxide and the solvent in the aqueous organic solvent system is acetone.
3. The process of claim 1 wherein there is one equivalent of the alkali metal hydroxide or carbonate.
4. The process of claim 1 wherein
R is isopropyl;
R$^3$ is

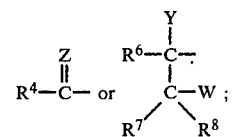

R$^4$ and R$^6$ are phenyl or mono-substituted phenyl; and
Z is oxygen or C$_1$–C$_7$ alkylidene.
5. The process of claim 4 wherein
R$^4$ and R$^6$ are phenyl;
Y and W together form a bond; and
Z is oxygen or ethylidene.
6. The process of claim 5 wherein R$^3$ is

and Z is oxygen.
7. The process of claim 6 wherein there is one equivalent of the alkali metal hydroxide or carbonate, which is sodium hydroxide, and the solvent in the aqueous organic solvent system is acetone.
8. The process of claim 5 wherein R$^3$ is

and Z is ethylidene.
9. The process of claim 8 wherein there is one equivalent of the alkali metal hydroxide or carbonate, which is sodium hydroxide, and the solvent in the aqueous organic solvent system is acetone.
* * * * *